United States Patent [19]

Arai et al.

[11] 4,342,744

[45] Aug. 3, 1982

[54] HAIR TREATMENT PRODUCTS

[75] Inventors: Masaaki Arai, Tocorozawa; Masami Ohba, Funabashi; Guy A. G. Ricketts, Tokyo, all of Japan; Jean A. Steer, Weybridge, England

[73] Assignee: Lever Brothers Company, New York, N.Y.

[21] Appl. No.: 167,978

[22] Filed: Jul. 14, 1980

[30] Foreign Application Priority Data

Jul. 19, 1979 [GB] United Kingdom ............... 7925174

[51] Int. Cl.$^3$ .......................... A61K 7/11; A61K 7/06
[52] U.S. Cl. ........................................ 424/70; 424/71
[58] Field of Search .................................. 424/70, 71

[56] References Cited

U.S. PATENT DOCUMENTS 3,101,301 8/1963 Siegal .................................... 424/70

FOREIGN PATENT DOCUMENTS 2206274 8/1973 Fed. Rep. of Germany .

Primary Examiner—Donald B. Moyer

[57] ABSTRACT

A hair treatment product comprises a polyvinyl pyrrolidone quaternized polymer and a phosphate mono-, di- or tri-ester and optionally a polyvinyl-pyrrolidone-vinyl acetate copolymer.

4 Claims, No Drawings

HAIR TREATMENT PRODUCTS

The invention relates to products for treating human hair in order to condition it and also to enable the hair to be set to a desired configuration.

In the conventional treatment of hair, conditioners can be applied to the hair, for example during or following a shampoo treatment, usually when the hair is in a wet state, in order to enable the hair to be combed out prior to styling. The hair can subsequently be set to a desired configuration after application of a setting aid. Usually the conditioner and the setting aid are applied separately since they can be incompatible if stored together as a single product, or since the benefit of the setting product can be diminished if the hair is too wet or is subsequently rinsed.

It has however been proposed in German Pat. No. 2206274 (J Singer) to apply to the hair a stable emulsion in water and/or alcohol containing as hair setting agents a copolymer of vinylpyrrolidone and vinyl acetate and also a quaternary polyvinylpyrrolidone polymer, together with an unspecified hair conditioning agent.

Clearly, it would be advantageous to the user if both conditioner and setting aid could be applied to the hair simultaneously, as this would reduce the number of steps that need to be employed in washing and restyling the hair. It is with the one-step conditioning and setting of the hair that the invention is concerned.

The invention is based on the discovery that deposition onto the hair of a polyvinylpyrrolidone quaternised copolymer in solution can be enhanced by including in the solution a phosphate ester. The hair can then be combed or brushed out when wet, or while being dried with hot or cold air without causing undue damage to the hair, as can occur if the hair is tangled. The combined use of the phosphate ester and the polymer also enables the hair to be set to a desired configuration without the problems of incompatability alluded to above. It has also been discovered that the setting of the hair to a desired configuration can further be improved by the additional incorporation in the hair treatment product of a polyvinylpyrrolidone-vinyl acetate copolymer, which is also free from the problem of incompatability with phosphate ester when functioning as a conditioner.

Accordingly, the invention provides a hair treatment product comprising:

(A) from 0.05% to 3% by weight of a polyvinyl-pyrrolidone quaternised copolymer; and
(B) from 0.2% to 3% by weight of a phosphate ester comprising a monoester of the formula

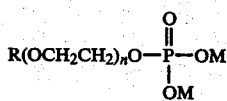

and/or a diester of the formula

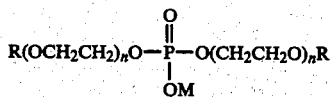

and/or a triester of the formula

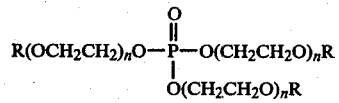

where
R is an hydrocarbon group having from 8 to 22 carbon atoms;
n is 0 or an integer of from 1 to 10; and
M is hydrogen or an alkali metal, ammonium or amine salt forming group.

The polyvinylpyrrolidone quaternised copolymer employed in the hair treatment product of the invention is a cationic polymer having a molecular weight which can exceed 1,000,000. Preferably, however, the molecular weight is less than 1,000,000. Examples of suitable quaternised copolymers are those marketed under trade names GAFQUAT 734 (low molecular weight) and GAFQUAT 755 (high molecular weight).

Although the quaternised copolymer functions primarily as a conditioning agent in that it makes combing of wet or dry hair easier, it will impart a certain degree of set to the hair. If, however, a more pronounced or durable set to the hair is required, it is possible optionally to include in the hair treatment composition one or more nonionic polymers of which polyvinylpyrrolidone vinyl acetate copolymers (PVP/VA) are preferred. Examples of the latter copolymers are LUVISKOL VA37E and LUVISKOL VA64E.

The hair treatment product will generally contain from 0.05% to 3%, preferably 0.1% to 1%, by weight of the quaternised copolymer and, if required, from 0.1% to 3% by weight of at least one of the nonionic copolymers.

Hair treatment products containing less than 0.05% by weight of the quaternised copolymer are unlikely in use to provide any noticeable improvement in conditioning properties, as compared with similar products from which the quaternised copolymer has been omitted. Furthermore, hair treatment products containing more than 3% by weight of the quaternised copolymer can in use result in the deposit of an excessive amount of the copolymer on the hair leading to flaking of the copolymer; the hair can then assume an unsightly appearance and can feel excessively sticky.

Similar considerations with respect to the nonionic copolymer can apply in that products containing less than 0.1% by weight are unlikely in use to result in an improvement in hold, whereas products containing more than 3% by weight can in use leave the hair unduly sticky and loaded with this copolymer, which may tend to flake off.

The phosphate ester of the product according to the invention comprises a monoester of the formula:

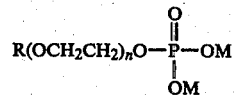

and/or a diester of the formula

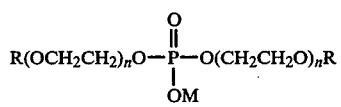

and/or a triester of the formula

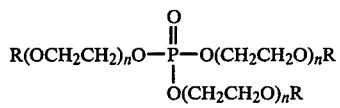

where
R is an hydrocarbon group having from 8 to 22 carbon atoms;
n is 0 or an integer of from 1 to 10; and
M is hydrogen or an alkali metal, ammonium or amine salt forming group.

The hydrocarbon group R is preferably one chosen from alkyl, alkenyl, cycloalkyl or cycloalkenyl groups.

When the group M is an alkali metal, it is preferably sodium or potassium, and when the group M is an amine salt forming group it can be a substituted ammonium group, particularly the lower alkyl and hydroxy lower alkyl groups, especially the mono-, di- and tri-ethyl, propyl, hydroxyethyl and hydroxypropyl-substituted ammonium groups.

The phosphate ester is usually produced commercially as a mixture of the mono- and/or di- and/or tri-esters defined above. They are available commercially under various trade mark names, for example BEROL, BRIPHOS, CRODAFOS and HOSTAPHAT. BEROL 729 has alkyl chain lengths of 16–18 carbon atoms and contains series of 4 ethylene oxide units. In BRIPHOS L2D the alkyl chains are lauryl groups and it contains series of 2 ethylene oxide units. In BRIPHOS O3D and CRODAFOS N3N the alkyl groups are oleyl and the ethylene oxide groups comprise 3 units. HOSTAPHAT KO3OON is a mixture of mono-, di- and tri-phosphoric esters of oleic acid. For mono- and di-phosphate ester mixtures, the weight ratio of monoester to di-ester may vary, typically from 1:10 to 10:1. Preferred phosphate esters are those in which n is 0 or an integer of from 1 to 6.

Phosphate ester is included in the product in an amount of 0.1% to 3% by weight of the product, preferably from 0.2% to 2.5% by weight.

Products containing less than 0.1% by weight of phosphate ester are unlikely in use to improve the deposition on the hair of copolymer beyond that which occurs when the phosphate ester is omitted altogether, while products containing more than 3% by weight of the phosphate ester may lead to competitive deposition of both copolymer and the phosphate ester leading to poor conditioning results.

The hair treatment product of the invention can also include minor amounts of other ingredients, for example, thickener, opacifier, perfume, colouring agent, preservative, proteins and an agent for adjusting pH, the latter usually being in the range 4 to 9, preferably from 5.5 to 7.5.

The hair treatment product can also comprise water, or an alcohol such as ethanol or isopropyl alcohol, or a mixture therefore, which can function as a carrier or a diluent for the active ingredients of the product. The water and/or alcohol can comprise up to 99% by weight of the product.

The hair treatment product, comprising the quaternised copolymer and phosphate ester, is primarily intended as an aid to combing out and styling hair which has been shampooed. It is therefore normally applied to the hair when the hair is in a wet state and when no further rinsing of the hair with water is intended. It is particularly usefully employed when the hair is to be dried with a hairdryer, while maintaining a brushing or combing action to detangle the hair as it dries just prior to styling. It is thus apparent that the product provides a surprising degree of protection to the hair when the hair is heated, as judged by the reduction in the damage to hair that can occur when simultaneously brushing out the hair and blow drying it with a hot air hairdryer. Accordingly, it is believed that the hair is rendered less brittle and prone to breakage under these conditions when the product of the invention has been applied.

When the hair treatment product additionally comprises the nonionic copolymer, it is preferably applied to shampooed hair after the final water rinse and immediately prior to combing out and styling while the hair is in a wet state, the styled hair then being dried, for example, with a hairdryer. The presence of the nonionic copolymer imparts to the hair additional setting and conditioning benefits.

The hair treatment product, either with or without the nonionic copolymer, can alternatively be applied directly to dry hair.

Evidence to support the improved conditioning properties as demonstrated by manageability and feel attributable to the hair treatment product of the invention is illustrated by the following experiment.

EXPERIMENT 1

Subjective assessment of hair treatment product

Materials and Method

Two test 'blow-dry' lotions having the following formulation were prepared:

|  | % w/w | |
| --- | --- | --- |
|  | A | B |
| GAFQUAT 755: 20% active | 0.6 | 0.6 |
| CRODAFOS N3N | — | 1.0 |
| Ethanol | 50 | 50 |
| Water | 49.4 | 48.4 |

Switches of dark hair (10 g and approximately 25 cm long) were shampooed, rinsed thoroughly with water and immersed in either of the two test lotions.

The switches were then subjected to a series of tests by a panel of trained assessors. All switches were tested according to standard procedures so as to avoid so far as was possible subjective variation. The nature of these subjective tests were as follows:

(1) Wet combability:
Switches were completely combed out and tangles removed in the wet state without water rinsing and the ease of combing was assessed for each switch.

(2) Dry combability:
Switches were dried with a hairdryer without prior wet combing. The ease with which each switch could be completely combed out and tangles removed was recorded.

(3) Least Flyaway:

Flyaway, that is the spreading apart of the 'open' end of the dry switch due to electrostatic charge was recorded: the smaller the spread the lower the flyaway value.

(4) Softness:

Dried switches were assessed by handling them and those switches which had a softer silkier feel to them were rated higher than those which were relatively harsher or more sticky to the touch.

(5) Stickiness:

Dried switches were also assessed by handling them for residual stickiness.

Results

The results are recorded in the Table below:

| Property | Preferred Product |
| --- | --- |
| Wet combability | B |
| Dry combability | B |
| Least flyaway | B |
| Softness | B |
| Stickiness | B = A |
| Overall preference | B |

These subjective evaluations indicate that the assessors preferred Product B (i.e. the product of the invention) to Product A for most of the properties examined, thus indicating that the presence of the phosphate ester imparted improvements to the manageability, appearance and feel of the hair over and above those attributable to the polyvinyl pyrrolidone quaternised copolymer alone.

Evidence to support the protection against damage when wet hair is brushed out during hot air drying can be obtained gravimetrically by collecting the hair which breaks from standard switches of hair following standard combing. An example of such an experiment is set out below.

EXPERIMENT 2

Evaluation of hair damage by brushing during hot air blow drying

Materials and Method

A test 'blow-dry' lotion having the following formulation was prepared:

| | % w/w C |
| --- | --- |
| GAFQUAT 734: 50% active | 0.4 |
| CRODAFOS N3N | 1.0 |
| Triethanolamine | 0.03 |
| Ethanol | 50.0 |
| Colour, perfume | qs |
| Water | to 100 |

Switches of dark hair (10 g and approximately 25 cm long) were shampooed, rinsed thoroughly with water and the test lotion, or water as a control, was applied to the switches.

All switches were then combed while being blow dried with a hot air dryer, using carefully controlled standard conditions so that each switch received exactly the same treatment. Hair which had broken free from the switches during combing was carefully collected and weighed.

Results

The results obtained are recorded in the Table below.

| Product | Weight of hair broken during brushing (mg) | % reduction of breakage due to product |
| --- | --- | --- |
| Blow Dry Lotion 'C' | 3.0 | 73 |
| Water (control) | 11.1 | 0 |

These results demonstrate that switches of hair which were treated with the product of the invention were protected against damage by breakage of the hair during combing to a substantial extent, as compared with switches of hair which were treated with water.

Evidence to support the conditioning benefit attributable to the presence of phosphate ester in a set lotion product which contained both quaternised and nonionic copolymers, can be derived from comparative subjective assessment of switches of hair which have been treated with differing lotions. An example of such an experiment is described below.

EXPERIMENT 3

Comparison of hair conditioning properties

Materials and Method

Two "set-lotions" having the following formulation were prepared:

| | % w/w | |
| --- | --- | --- |
| | C | D |
| GAFQUAT 755 | 0.5 | 0.5 |
| LUVISKOL 37E | 0.75 | 0.75 |
| LUVISKOL 64E | 0.75 | 0.75 |
| CRODAFOS N3N | — | 1.0 |
| Ethanol | 50.0 | 50.0 |
| Water | 48.0 | 47.0 |

Switches of dark hair (10 g and approximately 25 cm long) were shampooed, rinsed thoroughly with water, and either of the two test lotions was then applied to the switches.

The switches were then subjected to a series of tests by a panel of trained assessors according to the standard procedures described above under Experiment 1.

Results

The results obtained are recorded in the Table below.

| Assessors' preference for hair conditioning properties | |
| --- | --- |
| Property | Preferred Product |
| (1) Wet combability | C = D |
| (2) Dry combability | D |
| (3) Least flyaway | D |
| (4) Stickiness | D |
| (5) Softness | D |
| (6) Overall preference | D |

These results show that for properties assessed in the dry state, set lotion D containing the copolymers together with phosphate ester is preferred to set lotion C from which the phosphate ester was omitted.

The invention also provides a process for preparing a hair treatment product which comprises preparing a mixture of (A) from 0.05% to 3% by weight of a polyvinyl-pyrrolidone quaternised polymer; and (B) from 0.2% to 3% by weight of a phosphate ester as herein defined; and, optionally, (C) from 0.1% to 3% by weight of a nonionic polymer as herein defined.

The invention also provides a method of treating the hair which comprises applying to the hair an effective amount of the hair treatment product as herein defined and subsequently setting the hair to a desired style.

The invention also provides a closed container or dispenser containing the hair treatment product as herein defined. The container or dispenser can, for example, be a pump spray device or a pressurised pack aerosol can, a squeeze bottle or sprinkler, or simply a capped bottle or tube.

The invention is illustrated by the following Examples.

EXAMPLE 1

This Example illustrates a hair treatment product which provides both conditioning and a light set when applied to wet hair prior to blow drying.

|  | % w/w |
|---|---|
| Quaternised PVP copolymer (GAFQUAT 734): 50% active | 0.4 |
| Diethanolamine polyethylene oleylether phosphate (CRODAFOS N3N | 1.0 |
| Triethanolamine | 0.03 |
| Colourants | 0.0003 |
| Perfume | 0.2 |
| Ethanol (95%) | 50 |
| Water | to 100 |

The product had a pH of 7.5.

This product is particularly suited to application to the hair as a spray from a pump spray applicator.

EXAMPLE 2

This Example also illustrates a hair treatment product which provides both conditioning and a light set when applied to wet hair prior to blow drying.

|  | % w/w |
|---|---|
| Quaternised PVP copolymer (GAFQUAT 755): 20% active | |
| Diethanolamine polyethylene oleylether phosphate (CRODAFOS N3N0 | 1 |
| Triethanolamine | 0.059 |
| Colourants | 0.0004 |
| Perfume | 0.2 |
| Ethanol | 0.2 |
| Water | to 100 |

The product had a pH of 7.3.

This product is suitable for application to the hair from a capped container.

EXAMPLE 3

This Example illustrates a hair treatment product which provides both conditioning and a stronger set than either of the products described in Examples 1 and 2.

|  | % w/w |
|---|---|
| Quaternised PVP copolymer (GAFQUAT 755): 20% active | 0.5 |
| PVP/VA copolymer (LUVISKOL VA37E): 50% active | 0.75 |
| PVP/VA copolymer (LUVISKOL VA64E): 50% active | 0.75 |
| Diethanolamine polyethylene oleylether phosphate (CRODAFOS N3N) | 1 |
| Triethanolamine | 0.059 |
| Colourant, perfume | qs |
| Ethanol (98%) | 50 |
| Water | to 100 |

The product had a pH of 7.2.

This product was suited to application to the hair from a pump spray dispenser.

EXAMPLE 4

This Example illustrates a hair treatment product which provides both conditioning and a stronger set than either of the products described in Examples 1 and 2.

|  | % w/w |
|---|---|
| GAFQUAT 734: 20% active | 0.4 |
| LUVISKOL VA37E: 50% active | 0.75 |
| LUVISKOL VA64E: 50% active | 0.75 |
| CRODAFOS N3N | 1 |
| Triethanolamine | 0.03 |
| Colourant, perfume | qs |
| Ethanol (98%) | 50 |
| Water | to 100 |

The product had a pH of 7.2 and was suited to application to the hair from a pump spray dispenser.

What is claimed is:

1. A product for conditioning and setting hair which comprises:

(A) from 0.05% to 3% by weight of a polyvinylpyrrolidone quaternised copolymer; and (B) from 0.1% to 3% by weight of a phosphate ester comprising a monoester of the formula

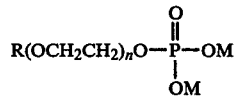

and/or a diester of the formula

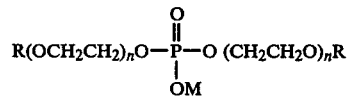

and/or a triester of the formula

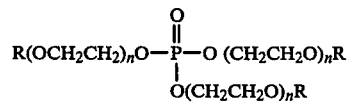

in which formulae R is an hydrocarbon group having from 8 to 22 carbon atoms, n is 0 or an integer of from 1 to 10 and M is hydrogen or an alkali metal, ammonium or amine salt-forming group.

2. A hair treatment product according to claim 1, further comprising from 0.1 to 3% by weight of a polyvinylpyrrolidone-vinyl acetate copolymer.

3. A hair treatment product consisting essentially of:

(A) from 0.1 to 1% by weight of a polyvinyl-pyrrolidone quaternised copolymer;

(B) from 0.2 to 2.5% by weight of a phosphate ester comprising a monoester of the formula

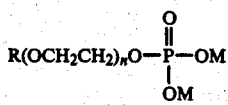

and/or a diester of the formula

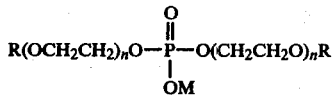

and/or a triester of the formula

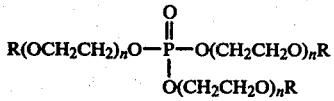

in which formula R is an hydrocarbon group having from 8 to 22 carbon atoms, n is 0 or an integer of from 1 to 10 and M is hydrogen or an alkali metal, ammonium or amine salt-forming group; and (C) water.

4. A method for conditioning and setting hair, which comprises applying to the hair the product according to claim 1, and subsequently setting the hair to a desired style.

* * * * *